United States Patent [19]

Shimamura et al.

[11] Patent Number: 5,639,455
[45] Date of Patent: Jun. 17, 1997

[54] IMMUNOSUPPRESSANT

[75] Inventors: Toshiro Shimamura; Harumi Nakazawa; Junji Hamuro, all of Kawasaki, Japan

[73] Assignee: Ajinomoto Co., Inc., Tokyo, Japan

[21] Appl. No.: 197,834

[22] Filed: Feb. 17, 1994

[30] Foreign Application Priority Data

Feb. 17, 1993 [JP] Japan .................... 5-028173

[51] Int. Cl.$^6$ .................... C07K 16/46; A61K 39/395
[52] U.S. Cl. .................... 424/133.1; 424/130.1; 424/141.1; 424/145.1; 514/8; 530/387.3; 530/388.23
[58] Field of Search .................... 435/69.6, 70.21, 435/69.7, 240.27, 172.2; 530/387.1, 388.23, 389.23, 866, 867; 514/8; 424/130.1, 145.1, 133.1, 141.1

[56] References Cited

U.S. PATENT DOCUMENTS 4,946,778  8/1990  Ladner et al. .................... 435/69.6

FOREIGN PATENT DOCUMENTS

| 0410813 | 1/1991 | European Pat. Off. . |
| WO91/07986 | 6/1991 | WIPO . |
| WO91/08774 | 6/1991 | WIPO . |

OTHER PUBLICATIONS

Waldmann [Science 252:1657–1662 (1991)].
Harris et al. [TIBTECH 11:42–44 (1993)].
Osband et al. [Immunotherapy 11(6):193–195 (1990)].
Dillman [Ann. Internal Med. 111:592–600 (1989)].
Hird et al. [Genes and Cancer (1990) chapter 17].
Curti [Critical Reviews in Oncology/Hematology 14:29–39 (1993)].
Genzyme [1993 Cataloge].
Crowther et al. [Ann. Oncol 2 supp 2:207–211 (1991) Medline abstract].
Digel et al. [Blood 78(3):753–759 (1991)].
Suzuki et al. [Eur. J. Immunol 22:1989–1993 (1992)].
Nature, vol. 347, pp. 497–498, Oct. 4, 1990, A. Pluckthun, "Antibodies From *Escherichia coli*".
The Journal of Biological Chemistry, vol. 266, No. 25, Sep. 5, 1991, Yves Laroche, et al., "Characterization of a Recombinant Single-Chain Molecule Comprising the Variable Domains of a Monoclonal Antibody Specific for Human Fibrin fragment D–Dimer", pp. 16343–16349.
Molecular Immunology, vol. 28, No. 11, pp. 1155–1161, Nov., 1991, Toshiro Shimamura, et al. "Analysis of Interleukin 6 (IL–60/IL–6 Receptor System Using Monoclonal Anti–IL–6–Antibodies".

*Primary Examiner*—Frank C. Eisenschenk
*Attorney, Agent, or Firm*—Oblon, Spivak, McClelland, Maier & Neustadt, P.C.

[57] ABSTRACT

Peptides which inhibit the binding of human IL-6 to human IL-6 receptor are useful as a treatment for diseases induced or aggravated by IL-6. DNA fragments, vectors, transformants, and methods useful for preparing such peptides are described.

4 Claims, 6 Drawing Sheets

FIG. 1a   5'- CAGGTGAAACTCGAGCAGTCAGG - 3'
              CC G     G   T

FIG. 1b   5'- AAGCTTCATGAGGAGACGGTGACCGTGGTCCC - 3'

FIG. 1c   5'- ACAGTCATAATGTCCCATATGGACATTCTGCTGACACAGTCTCCA - 3'
                    T  C  A A      C

FIG. 1d   5'- GCATCGTCGACTTTGAGCTCCAGCTTGGTCCC - 3'

(ClaI)           (NdeI) (SalI)
5'- CGATTAGTAAGGAGGTTTCATATGTCGACAAATCCTCAGGATCTGGCTCCGAATCCAAAA

3'-    TAATCATTCCTCCAAAGTATACAGCTGTTTAGGAGTCCTAGACCGAGGCTTAGGTTTT
             (XhoI) (HindIII) (BamHI)

GCACGCAGGTCAAACTCGAGAAGCTTG    - 3'

CGTGCGTCCAGTTTGAGCTCTTCGAACCTAG - 5'

FIG. 2

cDNA FRAGMENT CORDING FOR THE V REGION
OF THE L-CHAIN OF THE HH61-10 ANTIBODY
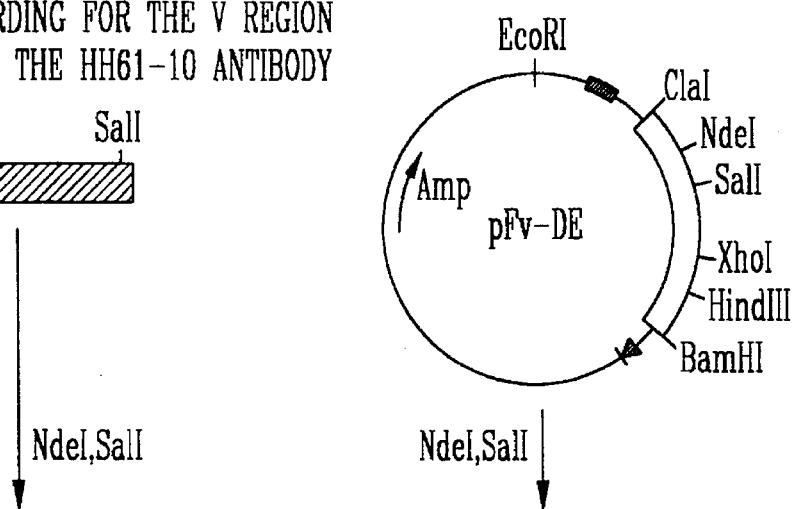
cDNA FRAGMENT CORDING FOR THE V REGION
OF THE H-CHAIN OF THE HH61-10 ANTIBODY
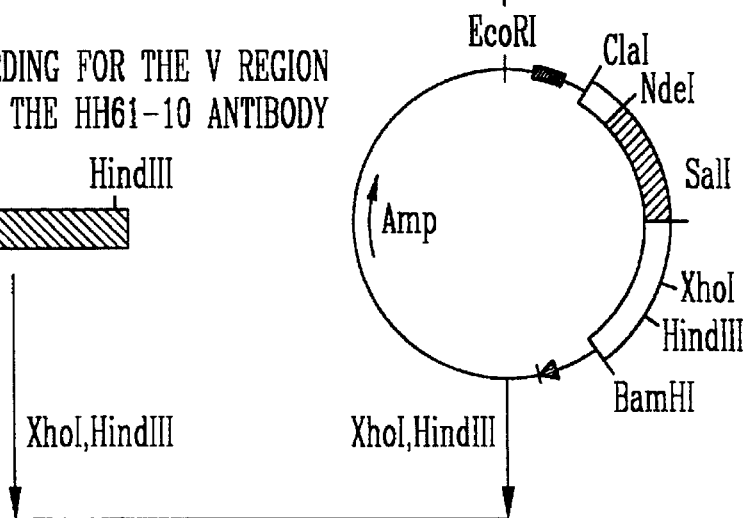
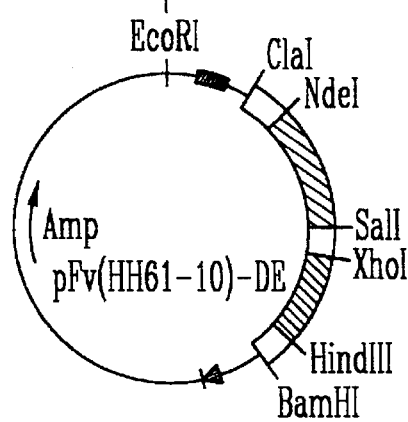
FIG. 4

IMMUNOSUPPRESSANT

BACKGROUND OF THE INVENTION

1. Field of the Invention

The present invention relates to a peptide which inhibits the binding of human IL-6 (interleukin-6) to human IL-6 receptor; to a human IL-6 suppressant, an anti-inflammatory agent, an immunosuppressant or an anti-autoimmune disease drug containing such a peptide; to a gene which encodes such a peptide; to a plasmid carrying such a gene; to a transformant containing such a plasmid; to a method for the production of such a peptide by culturing such a transformant; and to a method of treating various diseases by administering such a peptide or a pharmaceutical composition containing such a peptide.

2. Discussion of the Background

Human IL-6 is a substance whose gene was isolated in 1986 (*Nature*, vol. 324, p. 73 (1986)). Human IL-6 is produced by a number of different types of cells, including monocytes, T cells, B cells, vascular endothelial cells, fibroblasts, and the like, and is known to have a variety of physiological effects, such as the induction of the differentiation of B-cells into antibody-producing cells, the induction of acute phase protein synthesis by liver cells, the induction of the differentiation of cerebral nerve cells, the induction of the proliferation and differentiation of hematopoietic cells, etc. (Jikken *Igaku*, vol. 7, No. 1, (1989)). Also, attention is being given to the participation of human IL-6 in various diseases, and many reports have been published in regard thereto.

First, reports regarding its participation in autoimmune diseases, include a report that the human IL-6 concentration in the synovial fluid of chronic arthritic rheumatism patients is extremely high in comparison with that of osteoarthritis patients (*European Journal of Immunology*, vol. 18, p. 1797 (1988)), that the autoimmune disease symptoms were improved by removing the primary tumors of cardiac myxoma patients which constitutively produce IL-6 (*Proceedings of National Academy of Science, USA*, vol. 84, p. 228 (1987)), and that in the case of Castleman's disease which is characterized by high γ-globulinemia, a high concentration of human IL-6 was detected in the supernatant of affected lymph node tissue cultures (*Jikken Igaku*, vol. 7, p. 50 (1989)), etc., and of the so-called autoimmune diseases of which autoantibody production is thought to be a cause or aggravator, those with which IL-6 is strongly connected are thought to be the most dominant.

Furthermore, in the area of cancer, tumor cells taken from multiple myeloma patients constitutively produce IL-6, and their growth is further promoted by adding IL-6 thereto, which has led to a report that IL-6 is an autocrine growth factor for multiple myeloma (*Nature*, vol. 332, p. 83 (1988)), and to the suspicion that IL-6 is a growth factor for other blood tumors as well, including Lennert's T lymphoma, B-type chronic lymphocytic leukemia, etc. In addition, there is indication that the metastasis of different kinds of cancer cells to the liver in mouse models is correlated with the IL-6-producing capability of those cancer cell strains (*Japanese Journal of Cancer Research*, vol. 82, p. 1299 (1991)), and further indication of a strong correlation between IL-6 and cancer cachexia from the fact that high levels of IL-6 were shown to be present in the blood of tumor-bearing mice (*Journal of Immunology*, vol. 143, p. 162 (1989)), and that body weight loss occurred in nude mice which have been inoculated with CHO cells (Chinese hamster ovary cells) carrying the mouse IL-6 gene (*Endocrinology*, vol. 128, p. 2657 (1991)).

In the area of infections, there have been many reports regarding the connection between IL-6 and bacterial infection or viral infection, such as that the IL-6 concentration in the blood of patients with septic shock was extremely high, and patients with higher levels of IL-6 in the serum showed a lower rate of survival (*Journal of Experimental Medicine*, vol. 169, p. 333 (1989); Blood, vol. 74, p. 1704 (1989)), that the mononuclear cells of fetuses suffering from intraamniotic infection produced large amounts of IL-6 (*Clinical Immunological Immunopathology*, vol. 55, p. 305 (1990)), that IL-6 was present at high levels in the cerebrospinal fluid of patients infected with the human immunodeficiency virus (HIV) (*Journal of Neuroimmunology*, vol. 23, p. 109 (1989)), and that cells derived from Kaposi's sarcoma frequently seen in AIDS patients constitutively produced IL-6 or proliferated in an IL-6-dependent manner (*Proceedings of National Academy of Science, USA*, vol. 37, p. 4063 (1990)).

Furthermore, in the case of inflammatory diseases, the possibility has been suggested that IL-6 acts as an autocrine factor in mesangial proliferative glomerulonephritis, based on the fact that IL-6 was produced by mesangial cells derived from mesangial proliferative glomerulonephritis patients (*Journal of Immunology*, vol. 143, p. 3949 (1989)), and that the proliferation of mesangial cells was observed in IL-6 transgenic mice which constitutively express IL-6 in a B cell-specific manner (*Proceedings of National Academy of Science, USA*, vol. 86, p. 7547 (1989)). Also, high levels of IL-6 in the serum and IL-6 production in epidermal tissue have been reported in patients with psoriasis vulgaris, a disease involving the proliferation of keratinocytes (*Proceedings of National Academy of Science, USA*, vol. 86, p. 6367 (1989)). In addition, IL-6 is also said to contribute to the various symptoms of inflammation, such as fever, chills, malaise, etc. (*American Journal of Physiology*, vol. 258, p. 798 (1990)).

In addition to the diseases mentioned above, IL-6 is also suspected of playing a role in various other diseases, including Alzheimer's disease, amyloidosis, I-type diabetes, hyperlipidemia, osteoporosis, polycythemia vera, thrombocythemia, myocardial infarction, and the like.

Thus, human IL-6 is suspected of being a cause of numerous diseases, particularly inflammatory diseases and diseases involving the proliferation of lymphocytes, or there is a high possibility of human IL-6 being involved in the aggravation of such diseases. Therefore it is thought that suppression of the activity of human IL-6 may provide a treatment of those diseases.

In fact, regarding some of the above mentioned diseases, the suppression of IL-6 in mouse model experiments has led to improvement in the diseases. For example, it has been reported that, by the administration of anti-mouse IL-6 antibody or anti-mouse IL-6 receptor antibody, which have an effect of suppressing the activity of mouse IL-6, to mice inoculated with myeloma cells, it is possible to both suppress the growth of myeloma cells and raise the survival rate of the mice (*Journal of Experimental Medicine*, vol. 172, p. 997 (1990)); that the metastasis of tumor cells to the liver may be suppressed by the administration of anti-mouse IL-6 antibody (*Japanese Journal of Cancer Research*, vol. 82, p. 1299 (1991)); that even mice infected with a lethal dose of *E. coli* survive when they are preadministered anti-mouse IL-6 antibody which suppresses the activity of mouse IL-6 (*Journal of Immunology*, vol. 145, p. 4185 (1990)), that when anti-mouse IL-6 antibody which possesses mouse IL-6-suppressing activity is administered to mouse models which develop cachexia when inoculated with tumor cells, an improvement is observed not only in the weight loss, but also in the symptoms of the cachexia (*Journal of Clinical Investigation*, vol. 89, p. 1681 (1992)), etc. These facts directly indicate that IL-6 is connected with the above mentioned diseases. They also indicate that if the activity of human IL-6 can be suppressed, then a way may be provided for their treatment.

Methods which suppress the activity of human IL-6 include a variety of methods such as the inhibition of IL-6 production by IL-6-producing cells, inhibition of the binding of the IL-6 produced to receptors on the IL-6 response cells, and inhibition of IL-6 signals to IL-6 response cells. The methods of inhibiting the binding of human IL-6 to its receptors on the human IL-6 response cells are thought to be capable of selectively suppressing only the function of human IL-6 and thus, in consideration of their clinical application, to have the least number of side effects. Nevertheless, no medicines which specifically inhibit the binding of human IL-6 to human IL-6 receptors have been hitherto known other than mouse monoclonal anti-IL-6 antibody and mouse anti-IL-6 receptor antibody. However, these antibodies, which are the only ones known, are foreign proteins prepared from mouse hybridomas, and their constituent components are mouse proteins. Therefore, when they are administered to humans, an immune reaction is raised against the mouse protein, causing serious side effects such as anaphylactic shock, serum sickness, etc., and their effects are reduced due to the production of neutralizing antibodies against the mouse protein. Thus, the clinical application of mouse-derived antibodies for patients is fraught with difficulty. Therefore, at present no substances are known for the specific inhibition of the binding of human IL-6 to human IL-6 receptors which are suitable for clinical use, and thus it has been desired to develop clinically applicable medicines which inhibit the binding of human IL-6 to human IL-6 receptors as treatments for the above mentioned numerous diseases.

SUMMARY OF THE INVENTION

Accordingly, it is one object of the present invention to provide novel peptides which inhibit the binding of human IL-6 to human IL-6 receptor.

It is another object of the present invention to provide pharmaceutical compositions which are human IL-6 suppressants, anti-inflammatory agents, immunosuppressants, or autoimmune disease treatments, and which contain such a peptide.

It is another object of the present invention to provide a gene which encodes such a peptide.

It is another object of the present invention to provide a plasmid carrying such a gene.

It is another object of the present invention to provide a transformant carrying such a plasmid.

It is another object of the present invention to provide a method for the production of such a peptide by culturing such a transformant.

It is another object of the present invention to provide a method for the treatment of autoimmune diseases such as rheumatoid arthritis and systemic lupus erythematosus, the treatment of bacterial infections, the treatment of septic shock due to bacterial infections, the treatment of viral infections, the treatment of cancers such as multiple myeloma, the suppression of cancer metastasis, the amelioration of cancer cachexia, and the treatment of inflammatory diseases such as mesangial proliferative glomerulonephritis, by the administration of such a peptide or such a composition.

These and other objects, which will become apparent during the following detailed description, have been achieved by the inventors' discovery of the method, described below for preparing a peptide which inhibits the binding of human IL-6 to human IL-6 receptor, thus suppressing the function of IL-6.

In other words, the present invention provides a peptide which inhibits the binding of IL-6 to human IL-6 receptor; a human IL-6 suppressant, anti-inflammatory agent, immunosuppressant or autoimmune disease treatment containing such a peptide; a gene which encodes such a peptide; a plasmid carrying such a gene; a transformant containing such a plasmid; a method for the production of such a peptide by culturing such a transformant; and a method of treating various deseases by administering such a peptide or pharmaceutical composition containing such a peptide.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIGS. 1(a)–(d) show primer sequences used in the examples described below. FIG. 1(a) shows the 5' end primer of the H-chain, SEQ ID NO:1. FIG. 1(b) shows the 3' end primer of the H-chain, SEQ ID NO:2. FIG. 1(c) shows the 5' end primer of the L-chain, SEQ ID NO:3. FIG. 1(d) shows the 3' end primer of the L-chain, SEQ ID NO:4. The primers of FIGS. 1(a) and (c) are the mixture of 32 primers that are degenerate at the five indicated positions. The underlined sequence of the primer of FIG. 1(b) represents a termination codon;

FIG. 2 shows a linker DNA sequence for linking the V region of the L-chain and the V region of the H-chain, SEQ ID NO:5;

FIG. 4 shows a process for the construction of plasmid pFv(HH61-10)-DE;

DETAILED DESCRIPTION OF THE PREFERRED EMBODIMENTS

Figure 3:
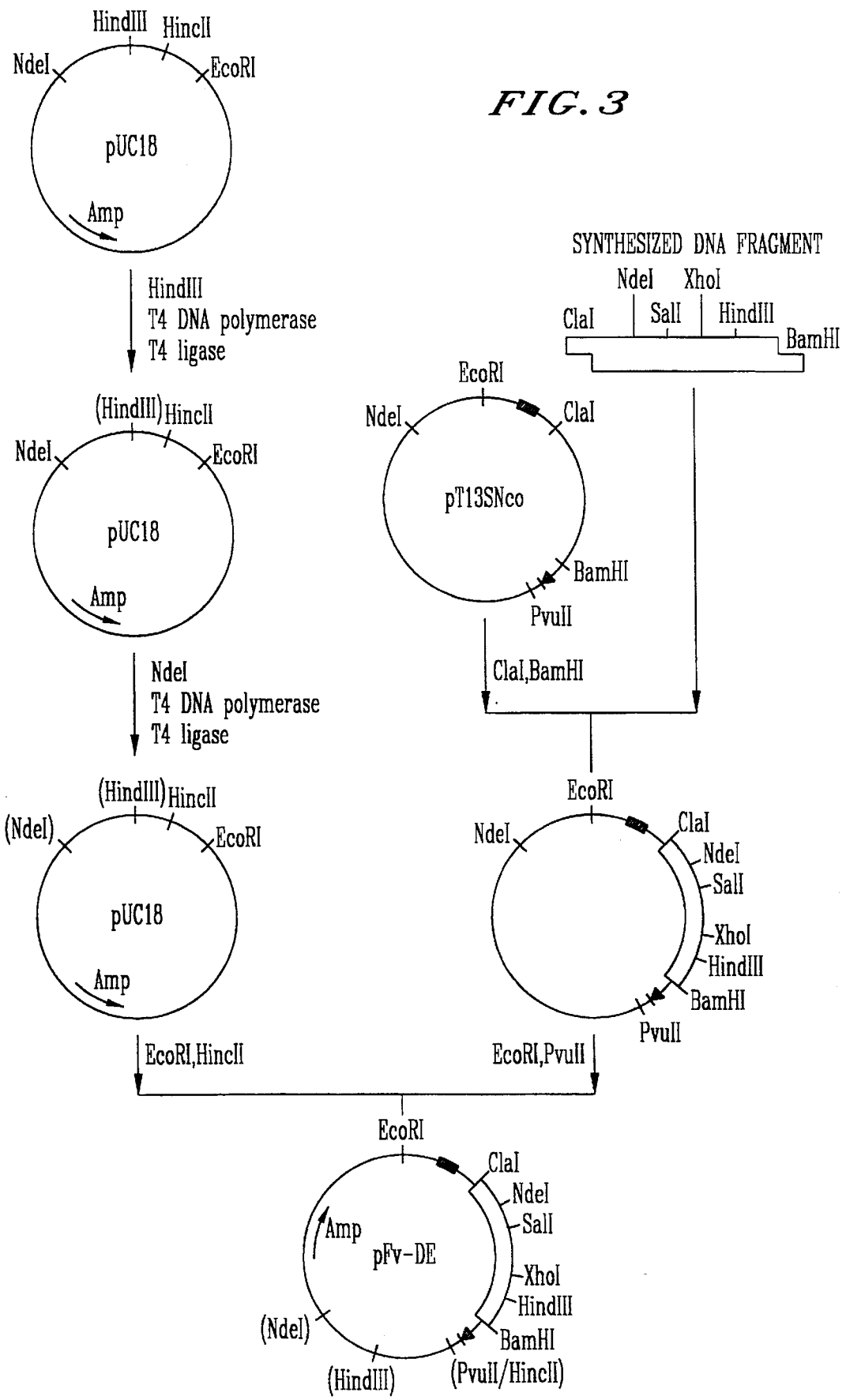
FIG. 3 shows a process for the construction of plasmid pFv-DE.

The peptide according to the present invention specifically inhibits the binding of human IL-6 to human IL-6 receptor to suppress the activity of IL-6, and it may be used as a treatment for autoimmune diseases such as rheumatoid arthritis, and systemic lupus erythematosus, a treatment for bacterial infections, a treatment for septic shock due to bacterial infections, a treatment for viral infections, a treatment for cancers such as multiple myeloma, a cancer metastasis suppressant, a medicine for the amelioration of cancer cachexia, and a treatment for inflammatory diseases such as mesangial proliferative glomerulonephritis. These applications are included in the terms human IL-6 suppressant, anti-inflammatory agent, immunosuppressant and autoimmune disease treatment, as used in the present specification.

Monoclonal antibodies which inhibit the binding of IL-6 to IL-6 receptors by binding to IL-6 or to IL-6 receptors are useful as binding inhibitors with extremely high specificity, but in general the monoclonal antibodies for molecules in humans are foreign proteins obtained by immunizing animals other than humans, such as mice. Therefore, when monoclonal antibodies are administered to the human body, antibodies are produced against the administered antibodies, and an immune reaction by way of phagocytes, the complement system, etc. is brought about, raising the possibility of shock symptoms known as allergy, serum sickness, and the like.

Antibody molecules are known to consist of variable regions (hereunder abbreviated as V regions) which contribute directly to the binding to the antigen, and constant regions (hereunder abbreviated as C regions) which perform the function of binding to phagocytes for their activation, activating complement, and giving rise to various immune reactions. Of these regions, the C regions constitute approximately ⅔ of the antibody molecule, and generally when they are administered to an animal of a different species, antibodies tend to be produced.

On the other hand, the inhibition of the binding of IL-6 to IL-6 receptors by anti-IL-6 antibody or anti-IL-6 receptor antibody requires the antigen-binding V regions of the antibody molecular structure, but the C regions of the antibody are not necessarily required. When the antibody containing the C regions is administered to the body, as described above, antibodies are produced against the antibody and form immune complexes with the antigen flowing in the blood, which can become trapped in the kidneys, etc. causing inflammation, or can bind with and be incorporated into phagocytes such as macrophages and the like, stimulating the release of inflammatory cytokines, chemical mediators, enzymes, etc. which further aggravate the inflammation. Therefore, it is preferred that the C regions not be present.

Antibody molecules assume a heterodimer structure in which H-chains (heavy chains) and L-chains (light chains) are bound to each other in the C regions via S—S bonds, and the H-chains are bound to each other in the C regions via S—S bonds, and therefore in order to produce an antibody molecule consisting of the V regions alone, there may be imagined a method whereby the V regions of the H-chains and L-chains of the antibody molecule are obtained by restrictive digestion of the antibody molecule using a proteolytic enzyme, after which they are bound together by some method to prepare a V region molecule consisting solely of a functional antibody, or a method whereby they are prepared by expressing the gene for the V regions of the H-chain and L-chain in a transformant using gene recombinant technology. However, with present technology, it is not possible by either method to efficiently and easily produce molecules consisting solely of the functional antibody V regions.

The present inventors have carried out a careful screening of monoclonal antibodies which are suitable for the following method and designed a single-chain peptide constructed from the V regions of the H-chains and L-chains of a few of the monoclonal anti-human IL-6 antibodies with a peptide linker using gene recombination technology, and have invented an efficient method for the production of a peptide which specifically inhibits the binding of human IL-6 to human IL-6 receptor, suppresses the activity of IL-6, and has a clear medicinal effect.

First, various types of hybridoma clones were prepared which produce mouse monoclonal antibodies which specifically bind to human IL-6 and inhibit the binding of human IL-6 and human IL-6 receptor, hence possessing the ability to suppress the activity of IL-6. The method for the preparation of the hybridoma clones producing mouse monoclonal anti-human IL-6 antibody is described below.

The hybridomas are prepared by fusing myeloma cells and antibody-producing cells. The antibody-producing cells may be spleen or lymph node cells from animals such as mice or rats which have been immunized with purified natural human IL-6 or recombinant human IL-6 produced using procaryotic cells such as *Escherichia coli* or the like, or eucaryotic cells such as yeast, animal cells, or the like.

The animal species from which the antibody-producing cells and myeloma cells are derived may be two different ones so long as both types of cells are fusible, but usually a more favorable result is obtained by using cells from the same species. One preferred hybridoma for carrying out the present invention is a hybridoma of (a) spleen cells or lymph node cells from mice which have been immunized with recombinant human IL-6 produced by *E. coli*, with (b) mouse myeloma cells.

For example, excellent results such as those demonstrated in the Examples which follow were obtained using hybridomas between spleen cells of Balb/c mice which were immunized with recombinant human IL-6 with Freund's complete adjuvant, and myeloma X63-Ag8-6.5.3 cells established from Balb/c mice.

The myeloma cells may be, in addition to X63-Ag8-6.5.3, 8-azaguanine-resistant cell strains, including SP2/0-Ag14, P3-X63-Ag8-U1, P3-X63-Ag8, P3-NSI/1-Ag4-1, MPC11-4.5.6.TG.1.7 (all mouse cells), 210.RCY.Ag1.2.3 (rat cells), SK0-007, GH15006TG-A12 (both human cells), etc.

The preparation of the hybridomas, and the selection therefrom of clones which produce monoclonal antibodies capable of binding to IL-6 and inhibiting the binding of IL-6 to IL-6 receptor for the suppression of the activity of IL-6 may be carried out, for example, in the following manner. The antibody-producing cells and the myeloma cells are fused together using polyethylene glycol or the Sendai virus, etc. Only the fused hybridomas are capable of growth in a culture medium containing hypoxanthine, thymidine and aminopterin (HAT medium). Not all of the resulting hybridomas produce antibodies, and not all of the antibody-producing hybridomas produce the desired antibody, and therefore it is necessary to select those hybridomas producing monoclonal antibodies which are capable of binding to IL-6 and inhibiting the binding of IL-6 to IL-6 receptor for the suppression of the activity of IL-6.

The selection may be made using, for example, the following method. That is, as the primary screening, a human-IL-6-coated plate is prepared and the hybridoma culture supernatant is reacted, and then $^{125}$I-labelled anti-mouse IgG is reacted, and those hybridomas with high binding amounts thereto are selected. As the secondary screening, the inhibiting activity against the binding of $^{125}$I-labelled IL-6 to IL-6 receptor-expressing cells and the inhibiting activity against the growth of cells whose growth is IL-6-dependent may be measured for the hybridoma culture supernatant, and those hybridomas with high levels of inhibiting activity selected.

The total RNA is then extracted from the hybridoma clones obtained in this manner, and the gene (cDNA) coding for the V regions of the monoclonal antibody is obtained. The present inventors have diligently devised a method to quickly obtain the object cDNA, and thus the cDNA which codes for the V regions of the antibody has been obtained in the following manner.

That is, first, nucleotide sequences of 20–30 bases (primer DNA) with a high degree of correspondence to the 5' end and 3' end, respectively, of the gene coding for the V regions, are designed based on the nucleotide sequence for the H-chains and L-chains of mouse IgG, whose genetic nucleotide sequences have already been published.

Here, the 5' end primer is designed in the 5'→3' direction, and a translation initiation codon, ATG, is attached at the 5' end of the L-chain V region primer. For the 3' end primer, a translation termination codon is attached at the 3' end of the primer for the H-chain, that is, the chain for which no ATG sequence has been attached. In the case of the 3' end primer, the complementary sequence may be redesigned in the 3'→5' direction.

Naturally, an ATG sequence may be attached at the 5' end of the H-chain V region primer, and a termination codon attached at the 3' end of the L-chain V region primer. As the termination codon may be used TAA, TAG or TGA. In the Examples according to the present invention, TGA was used as the termination codon.

Next, an appropriate restriction enzyme site is introduced at the 5' end of the primer DNA of the respective H-chains and L-chains (in the case of the 3' end primer, at the 5' end of the redesigned primer DNA), for insertion into an expression vector. The designed primer DNA is chemically synthesized using a DNA synthesizer or the like.

Further, the total RNA is extracted from the resulting hybridomas by a conventional method, single-stranded cDNA is prepared using reverse transcriptase and the 3' end primer DNA, and then, using the 5' end primer DNA and the 3' end primer DNA, the DNA fragments coding for the V regions of the H-chain and L-chain of the antibody are obtained by their selective amplification by the Polymerase Chain Reaction (PCR method; *Science*, vol. 230, p. 1350 (1985)) using Taq polymerase.

When the obtained genes coding for these V regions are expressed in *E. coli* to prepare functional antibody V region molecules, the respective genes may be incorporated separately or simultaneously into a single vector, and then assembled for expression, but the efficiency of this method is known to be extremely poor (*Science*, vol. 240, p. 1038 (1988)).

Recently, a technique has been developed whereby the V regions are linked together using a linker, and are thus expressed in *E. coli* as a single chain molecule (*Science*, vol. 242, p. 423 (1988)). The present inventors, have applied this technique, and through further manipulation and improvement, have succeeded in expressing a single peptide chain consisting of the V regions of human IL-6 antibody, and in maintaining and even improving the properties with no loss of the function to inhibit the binding of human IL-6 to human IL-6 receptor.

In other words, first, an expression vector is constructed to include, in the following order from upstream, a promoter, a ribosome-binding site, a restriction enzyme site which corresponds to the restriction enzyme site which has been introduced into the 5' end primer with an ATG sequence attached thereto, a restriction enzyme site which corresponds to the restriction enzyme site which has been introduced into the 3' end primer of the same chain, a DNA sequence coding for a linker peptide of suitable length for joining the V region of the antibody L-chains and the V region of the antibody H-chains, a restriction enzyme site which corresponds to the restriction enzyme site which has been introduced into the 5' end primer with no ATG sequence attached thereto, a restriction enzyme site which corresponds to the restriction enzyme site which has been introduced into the 3' end primer of the same chain, and finally a terminator.

Here, when introducing the DNA of each V region which was amplified by the PCR, care should be taken so that the translation of the linker peptide and the following V region DNA is not shifted.

For the present invention, the source from which the promoter is derived is not critical, and for example, trp promoter, tac promoter, trc promoter, lac promoter from *E. coli* and $\lambda P_L$ promoter, $\lambda P_R$ promoter from $\lambda$-phage, etc. may be used. The ribosome-binding site to be used may be the ribosome-binding site of trpL, trpE or lacZ from *E. coli* or of CII protein from $\lambda$-phage. Alternatively, a chemically synthesized DNA sequence may be used. In addition, for a large accumulation of the object peptide in a granular form in *E. coli*, 2 or more ribosome-binding sites may be employed.

The linker peptide sequence for joining the respective antibody V regions together may be any one so long as the prepared antibody V region molecule is functional, but in order to minimize the side effects of the molecule when administered to the human body, the sequence is preferably as short as possible and with no unique structure. Furthermore, manipulation is required to ensure that, once the peptide is expressed, the function of the V regions is not lost or attenuated. Typically, the linker peptide is 10 to 20, preferably 12 to 16, amino acid residues long. The terminator to be used may be, for example, trpA terminator, rrnB terminator, recA terminator, etc. from *E. coli*. Also, usually a larger number of copies of the expression plasmid is preferred, and the replication origin is preferred to be pUC rather than pBR.

The PCR-amplified DNA for each of the H-chain and L-chain V regions is then inserted into the constructed expression plasmid. After the insertion, the expression plasmid may be used to transform a host by a conventional method, and then expressed. The host may be any procaryotic or eucaryotic organism. Examples of procaryotic organisms include *E. coli*, *Bacillus subtilis*, etc. The eucaryotic cells to be used may be, for example, yeast, CHO cells, or the like. Procaryotic cells, and particularly *E. coli*, are preferred for use as the host.

The method of incorporating the expression vector into these hosts may be any conventional method; for example, one in which *E. coli* cells in the logarithmic growth phase are treated with 50 mM of calcium chloride on ice for about 30 minutes to modify the structure of the cell wall of *E. coli*, and then 10 minutes after the plasmid DNA is injected thereinto the cells are subjected to heat treatment at 30°–42° C. for 2 minutes, after which a culture medium is added thereto for culturing at 30°–37° C. for about 60 minutes, to incorporate the expression plasmid DNA into the organism.

By culturing these cells, the object peptide which inhibits the binding of human IL-6 to human IL-6 receptor may be accumulated either in the cells themselves or in the culture medium. The medium may be any of a number of conventionally known ones in which the culturing of cells is possible, and the culturing conditions may be any conventionally known ones. After the culturing, the object peptide may be recovered by a conventional method.

The peptide according to the present invention possesses activity to inhibit the binding of human IL-6 to human IL-6 receptor for the suppression of the activity of human IL-6, and thus it is an effective substance for use as a treatment for autoimmune diseases such as rheumatoid arthritis and systemic lupus erythematosus, a treatment for bacterial infections, a treatment for septic shock due to bacterial infections, a treatment for viral infections, a treatment for cancers such as multiple myeloma, a cancer metastasis suppressant, a medicine for the amelioration of cancer cachexia, and a treatment for inflammatory diseases such as mesangial proliferative glomerulonephritis, and other diseases thought to be induced or aggravated by IL-6.

Furthermore, the structure of the peptide according to the present invention is not limited to the sequence listed as SEQ ID NO:6 in the Sequence Listing, as the peptide according to the present invention includes any peptide which possesses activity to inhibit the binding of human IL-6 to human IL-6 receptor for the suppression of the activity of human IL-6. For example, included in the peptide according to the present invention are (1) a linear or cyclic peptide lacking one or more, preferably less than 15, amino acids from the N-terminus and/or C-terminus of the peptide structure listed as SEQ ID NO:6 and has a continuous amino acid sequence, (2) a peptide having a structure wherein one or more, preferably less than 70, amino acids in the peptide structure listed as SEQ ID NO: 6 are replaced with other amino acids, (3) a peptide having a structure wherein one or more, preferably less than 500, amino acids are added at the N-terminus and/or C-terminus of the peptide structure listed as SEQ ID NO:6, and (4) a peptide having a structure wherein one or more, preferably less than 70, amino acids of the peptide listed as SEQ ID NO:6 are acetylated, amidized or polyethylene glycol-added, so long as the peptide possesses the ability to inhibit the binding of human IL-6 to human IL-6 receptor for the suppression of the activity of human IL-6.

By the ability to inhibit the binding of human IL-6 to human IL-6 receptor to suppress the activity of IL-6, it is meant that the peptide (i) causes at least a 50% reduction in the binding of $^{125}$I-IL-6 to U266 cells as measured by the procedure described in the examples below at a concentration of 10 μg/ml; (ii) causes at least a 50% reduction in the proliferation of KT-3 cells as measured by the procedure described in the examples below at a concentration of 8.0 μg/ml; or (iii) causes at least a 50% reduction in the production of haptoglobulin as measured by the procedure described in the examples below at a concentration of 20 μg/ml.

In particular, the N-terminal Met of the peptide listed as SEQ ID NO:6 in the Sequence Listing is sometimes cut off during the process of expression by a microorganism or purification, leaving Asp at the N-terminus. Such a peptide is also included in the peptide according to the present invention so long as it possesses the activity mentioned above. In addition, a peptide prepared by removing the N-terminal Met from the resulting Met-bonded peptide using amino peptidase or the like is also included in the peptide according to the present invention so long as it possesses the activity mentioned above.

Furthermore, peptides prepared by converting the so-called framework regions of the peptides according to the present invention into human-derived frameworks are naturally expected to possess the same activity as the peptides prior to the conversion, and thus they are also included in the peptide according to the present invention, so long as they possess the activity mentioned above.

In addition, if necessary a peptide prepared by adding a toxin to the peptide according to the present invention may be used. Such toxins may be covalently bound to the peptide of the present invention by conventional means, e.g., a crosslinking agent.

An immunosuppressant according to the present invention contains the above-mentioned peptide in a proportion of 0.1–100 wt %, or preferably 0.5–70 wt %, based on the total weight of the immunosuppressant. Therefore, the peptide according to the present invention may be administered directly or in the form of a composition thereof made by mixing it with a pharmaceutically acceptable carrier. The pharmaceutically acceptable carrier to be used may be any commonly used substance which does not react with the peptide according to the present invention. In the case of an injection, the peptide according to the present invention is prepared for use by dissolution in water, and if necessary it may be dissolved in physiological saline or a glucose solution, and it may contain a buffering agent, preservative, stabilizer or diluent. In addition, these preparations may also contain other components with therapeutic value.

The method for administration of the immunosuppressant according to the present invention may be oral, by injection, intrarectal, etc., but administration by injection is preferred. The dosage will differ depending upon the method of administration and the symptoms, age, etc. of the patient, but normally it is 0.001–1000 mg for a single dose, and preferably 0.01–10 mg administered 1–3 times per day.

Other features of the invention will become apparent in the course of the following descriptions of exemplary embodiments which are given for illustration of the invention and are not intended to be limiting thereof.

EXAMPLES

Example 1

(Preparation of hybridomas):

Six to 8-week-old female BALB/c mice were immunized by subcutaneous administration of 100 μg/mouse of recombinant human IL-6 with Freund's complete adjuvant. Three weeks afterwards, they were subjected to booster immunization in the same manner, and then 5 days afterwards blood was taken from the orbital vein, and, following the method described below, the IL-6-binding activity thereof was tested to determine the antibody titer. The recombinant human IL-6 (2 μg/ml) dissolved in phosphate buffered saline (PBS) was separately placed in the wells of 96-well microtiter plates (product of Flow Co.), and left to stand overnight at 4° C. The plates were then treated with PBS containing 0.5% bovine serum albumin (BSA-PBS), and incubated for 1 hour at room temperature. Sample sera diluted to an appropriate concentration with BSA-PBS were added to each well and incubated for 2 hours at room temperature. After washing the plates with PBS containing 0.05% Tween-20 (product of Nacalai tesque Co.) (PBS-Tween), anti-mouse Ig antibody (product of Daco Co.) was added to each well, followed by incubation for 2 hours at room temperature. Then the plates were washed with PBS-Tween, and 2,2'-azino-bis(3-ethylbenzothiazoline-6-sulfuric acid) (ABTS); product of Sigma Co.) and hydrogen peroxide were added to each well and the absorbance (A405) of the wells were measured. Mice with a high antibody titer were further subjected to a final immunization in the same manner, and 3 days afterwards the spleens were extracted, and the spleen cells and mouse myeloma cells (X63-Ag8-6.5.3) were mixed together in the presence of 50% polyethylene glycol #4000 (product of Nacalai tesque Co.) to a cell count proportion of 10:1, for fusion of the cells.

The fused cells were suspended in an RPMI1640 culture medium (product of Gibco Co.) containing 10% bovine calf serum (product of Gibco Co.) to a cell concentration of $5 \times 10^6$ cells/ml, and a 100 μl portion thereof was poured into each well of a 96-well flat-bottom plate (product of Corning Co.) which contained $5 \times 10^5$ mouse thymus cells per well. At 1, 2, 3 and 6 days afterwards, half of the culture medium was replaced with a medium containing hypoxanthine, aminopterin, and thymidine (HAT medium), and the process was repeated every 3 days thereafter. The culture supernatant of each well in which the fused cells (hybridomas) had grown was tested, and those hybridomas in the wells which possessed IL-6-binding activity were cloned by the limiting dilution method.

In addition, the IL-6-binding activities of culture supernatants of each of the hybridoma clones were determined, and the anti-IL-6 antibody-producing hybridomas were obtained. Further, the culture supernatants of the obtained anti-IL-6 antibody-producing hybridomas were tested for suppression of the activity of IL-6, using the following method. A 50 μl portion of a human recombinant IL-6 solution prepared with a concentration of 200 pg/ml in an RPMI1640 culture medium containing 10% bovine calf serum was poured into each well of a 96-well flat-bottom microplate, 50 μl of one of the sample culture supernatants was added thereto, and the cells were incubated at 37° C. for 30 minutes. Also, 100 μl of an MH60 cell suspension in an RPMI1640 culture medium containing 10% bovine calf serum to a concentration of $1 \times 10^5$ cells/ml was added to each well, and the cells were cultured at 37° C. for 3 days, in the presence of 5% $CO_2$. For the final 6 hours, the culturing was carried out with addition thereto of 1 μCi of $^3$H-thymidine (product of DuPont Co.), and the amount of radioactivity taken into the cells was measured using a scintillation counter (product of Packard Co.) to determine the activity of suppression of the activity of IL-6 for the culture supernatant. Thus were prepared hybridomas producing antibodies against IL-6. One of the hybridomas obtained in this manner is HH61-10 (see Japanese Patent Application Disclosure HEI 3-61496).

Example 2

(Preparation of antibody V region cDNA from the hybridomas):

Of the hybridoma HH61-10 cells, $5 \times 10^6$ were washed with PBS, and an RNA extraction buffer solution (product of Pharmacia Co.) containing guanidine thiocyanate, N-lauryl sarcosine and EDTA was added thereto to prepare a suspension, which was then overlayed on an equivolume of cesium chloride solution (ρ=1.51 g/ml, product of Pharmacia Co.) provided beforehand in a tube and subjected to centrifugation at 125,000×g for 16 hours. After the supernatant thereof was sucked off, a 10 mM Tris-HCl buffer solution containing 1 mM of EDTA (pH 7.5) was added to the residue to prepare a suspension, which was poured into a fresh tube, for incubation at 65° C. for 5 minutes. In addition, a 1/10 volume of 2M potassium acetate (pH 5.0) (product of Pharmacia Co.) and a 3-fold volume of ethanol (product of Nacalai tesque Co.) were added thereto, and the mixture was allowed to stand at −20° C. overnight. It was then subjected to centrifugation at 5,000×g for 20 minutes and the supernatant thereof discarded, after which the residue was subjected to centrifugal washing with 80% ethanol, and the resulting precipitate was dried. The precipitate was dissolved in a 10 mM Tris-HCl buffer solution containing 1 mM of EDTA (pH 7.5) to prepare a solution of the total RNA fraction.

Next, to the total RNA fraction solution were added a solution containing a predesigned primer complementary to the 3' end of the gene for the V regions of the H-chains and L-chains of the antibody (final concentration: 1 μM), a mixed solution of deoxyNTP, a buffer solution for cDNA synthesis (product of Amersham Co.), RNAse inhibitor (product of Takara Shuzou Co.) and reverse transcriptase (product of Takara Shuzou Co.), and these were reacted at 42° C. for 1 hour to synthesize the cDNA. In addition, a PCR buffer solution (product of Cetus Co.), a mixed solution of deoxyNTP, 5' end primer and 3' end primer for amplification of the V regions of the H-chains and L-chains of the antibody (both final concentrations: 1 μM) and Taq polymerase (product of Takara Shuzou) were added thereto for the PCR (thermal cycler, product of Cetus Co.). The reaction was carried out with 30 cycles each consisting of denaturing for 30 seconds (94° C.), annealing for 30 seconds (55° C.) and primer extension for 1 minute (72° C.), and each cycle the primer extension time was lengthened by 15 seconds.

After the reaction, the product was subjected to agarose gel electrophoresis in a 40 mM Tris-HCl-acetate buffer solution containing 1 mM of EDTA (pH 8.0), and the object cDNA fragments were cut out and then extracted and purified using a gene clean kit (product of Bio 101 Co.). The sequences of the primers used for the synthesis of the cDNA and the PCR are shown in FIGS. 1(a)–(d) (SEQ ID NOS:1–4).

Example 3

(Construction of the expression vector):

As shown in FIG. 3, first the large DNA fragments obtained by cleaving pT13SNco (E. coli AJ-12447 containing this plasmid has been deposited as FERM P-10757) [listed in J. Biochem., vol. 104, p. 30 (1988)] with restriction enzymes ClaI and BamHI (both products of Takara Shuzou Co.) and a conventionally prepared synthesized DNA fragment (linker) having the sequence shown in FIG. 2 (SEQ ID NO:5), were linked using T4DNA ligase (product of Takara Shuzou Co.).

Next, also as shown in FIG. 3, the synthesized DNA fragment was linked with the larger fragment obtained by cleaving the plasmid pT13SNco with restriction enzymes ClaI and BamHI. A plasmid pFv-DE having a pUC origin of replication was obtained by using T4 ligase to ligate the smaller DNA fragment obtained by cleaving the previously mentioned linked plasmid with restriction enzymes EcoRI and PvuII (both products of Takara Shuzou Co.) with the larger DNA fragment obtained by using EcoRI and HindII (products of Takara Shuzou Co.) to cleave plasmid pUC18 (Methods in Enzymology, vol. 101, p. 20 (1983)) whose HindIII and NdeI sites had been removed by cleavage with the corresponding restriction enzymes and then making the ends blunt with T4 DNA polymerase (product of Takara Shuzou Co.), and finally ligating them with T4 ligase.

Example 4

(Insertion of antibody V region cDNA into pFv-DE and preparation of a E. coli strain producing antibody consisting solely of the V regions):

As shown in FIG. 4, first T4 ligase was used to ligate the larger DNA fragment obtained by cleaving pFv-DE with restriction enzymes NdeI and SalI (products of Takara Shuzou Co.) with the fragment obtained by cleaving the L-chain V region cDNA of HH61-10 recovered after the PCR using the same restriction enzymes NdeI and SalI. The L-chain V region of HH61-10 corresponds to the 4th–324th bases of the nuceotide sequence listed as SEQ ID NO:6 in the Sequence Listing. In both sequences, the 1st–3rd bases of the sequence are the translation initiation codon ATG.

Next, T4 ligase was used to ligate the larger DNA fragment obtained by further cleaving the above ligated plasmid with restriction enzymes XhoI and HindIII (products of Takara Shuzou Co.) with the fragment obtained by cleaving the H-chain V region cDNA of HH61-10 recovered after the PCR using the same restriction enzymes XhoI and HindIII, in order to construct and obtain a plasmid pFv (HH61-10)-DE expressing an antibody consisting solely of the V regions. Next, each of the plasmids was used to transform $E.$ $coli$ HB101 strain to obtain a strain producing antibody consisting solely of the V regions ($E.$ $coli$ pFv (HH61-10)-DE/HB101, AJ-12789, FERM BP-4523).

The H-chain V region of HH61-10 corresponds to the 367th–738th bases of the nucleotide sequence listed as SEQ ID NO: 6 in the Sequence Listing.

Example 5

(Acquisition of product from the strain producing antibody consisting solely of the V regions):

Cultures of the microorganism $E.$ $coli$ pFv (HH61-10)-DE/HB101 were deposited with Fermentation Research Institute, Agency of Industrial Science and Technology (1–3, Higashi, 1-chome, Tsukuba-shi, Ibaraki-ken 305, Japan) under the deposit number of FERM BP 4523 on Jan. 5, 1994.

The resulting transformant $E.$ $coli$ pFv (HH61-10)-DE/HB101 (FERM BP-4523) was grown overnight at 37° C. in 5 ml of 2×YT [1.6 % trypton, 1% yeast extract (both products of Bacto Co.), 0.5% NaOH, pH 7.0] containing 50 µg/ml of ampicillin. Next, 5 ml of the culture suspension was seeded into 100 ml of an M9-casamino acid culture medium (0.6% $Na_2HPO_4 \cdot 12H_2O$, 0.3% $KH_2PO_4$, 0.05% NaCl, 0.1% $NH_4Cl$, 0.05% $MgSO_4 \cdot 7H_2O$, 0.00147% $CaCl_2$, 0.2% glucose, 0.2% of casamino acid, 0.02% L-leucine, 0.02% L-proline, 0.0002% thiamine hydrochloride, 100 µg/ml ampicillin, pH 6.9), for culturing at 37° C. for 3 hours. Following this, 3-indoleacrylic acid (IAA) was added thereto to a concentration of 25 µg/ml, and induction culturing was continued at 37° C. for 20 hours. A portion of this cell suspension was observed using a phase contrast microscope at about 1500×magnification, and inclusion body formation was found in the $E.$ $coli$ cells.

Next, the cell suspension which was cultured in the manner described above was subjected to centrifugal separation and the cells thereof collected, and 50 ml of a 20 mM Tris-HCl buffer solution containing 30 mM of NaCl (pH 7.5) was added thereto to form a suspension, after which 12.5 ml of a solution of lysozyme in 0.5M EDTA (pH 8.0) at a concentration of 1 mg/ml was added thereto and the mixture was stirred and then allowed to stand on ice for 1 hour. Next, the cells were disrupted ultrasonically, and then subjected to centrifugal separation at 6,000 rpm for 5 minutes, after which the inclusion bodies were collected. The inclusion bodies were solubilized with 6M guanidine hydrochloride, and adjustment was made for a 100 µg/ml concentration of the object peptide and a 3.5M guanidine hydrochloride solution, after which 3 µM of oxidized glutathione and 30 µM of reduced glutathione were added thereto, and the mixture was allowed to stand at a pH of 8.0, at room temperature for 10–16 hours. Then, the mixture was dialyzed against a 10 mM acetate buffer solution (pH 5.0) to obtain the crude peptide.

Next, the crude peptide was passed through an S-Sepharose column (product of Pharmacia Co.) which had been equilibrized in advance with a 10 mM acetate buffer solution (pH 5.0), and then eluted with a 10 mM acetate buffer solution containing 50 mM of NaCl (pH 5.0), after which the eluate was dialyzed against PBS to obtain the object peptide.

The molecular weight of this substance determined according to SDS-polyacrylamide gel electrophoresis roughly matched the value obtained by calculation based on the amino acid sequence deduced in Example 6, and as a result of investigation of the N-terminal amino acid sequence using a protein sequencer, confirmation was made of the sequence having methionine added to the N-terminus of the deduced amino acid sequence.

Example 6

(Determination of the nucleotide sequence and deduction of the amino acid sequence):

The constructed plasmid pFv(HH61-10)-DE expressing the peptide consisting solely of the V regions connected by a linker was purified by the alkali SDS method, and commercially available M4 or RV primer for sequencing (products of Takara Shuzou Co.) were used to determine the nucleotide sequence with a 7-DEAZA sequencing kit (product of Takara Shuzou Co.). The amino acid sequence was deduced from the obtained nucleotide sequence.

The nucleotide sequence coding for the peptide Fv(HH61-10) and the amino acid sequence corresponding thereto are listed as SEQ ID NOS: 6 and 7, respectively, of the Sequence Listing. That is, as shown in SEQ ID NO:7 of the Sequence Listing, the peptide Fv(HH61-10) is a peptide comprising 246 amino acids, having Met at the N-terminus and Ser at the C-terminus.

Example 7

(Detection of the activity of peptide Fv(HH61-10)):

(1) Inhibiting activity against binding of IL-6 to IL-6 receptor

Figure 5:
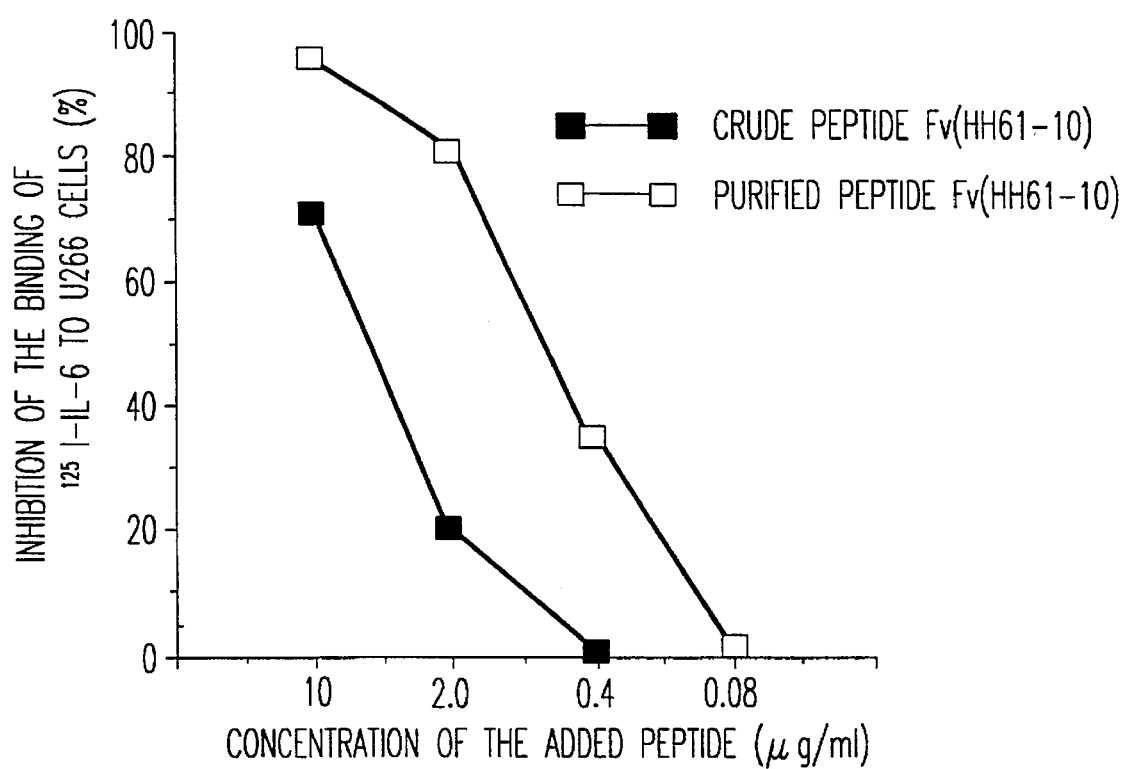
FIG. 5 shows the inhibition of the binding of $^{125}$I-labelled IL-6 to U266 cells by the peptide Fv(HH61-10)

The peptide Fv(HH61-10) diluted to an appropriate concentration with an RPMI1640 medium containing 0.5% BSA and 0.02% $NaN_3$ was mixed with human recombinant IL-6 which had been $^{125}$I-labelled by the Bolton-Hunter method, and these were reacted at room temperature for 1 hour. After the reaction, $5 \times 10^5$ U266 cells suspended in the same medium were added thereto for reaction at 4° C. for one hour, and the radioactivity which had bound to the cells was measured. As shown in FIG. 5, it was clear that the peptide Fv(HH61-10) inhibits the binding of human IL-6 to human IL-6 receptor.

(2) Inhibiting activity against growth of IL-6-dependent cell line

Figure 6:
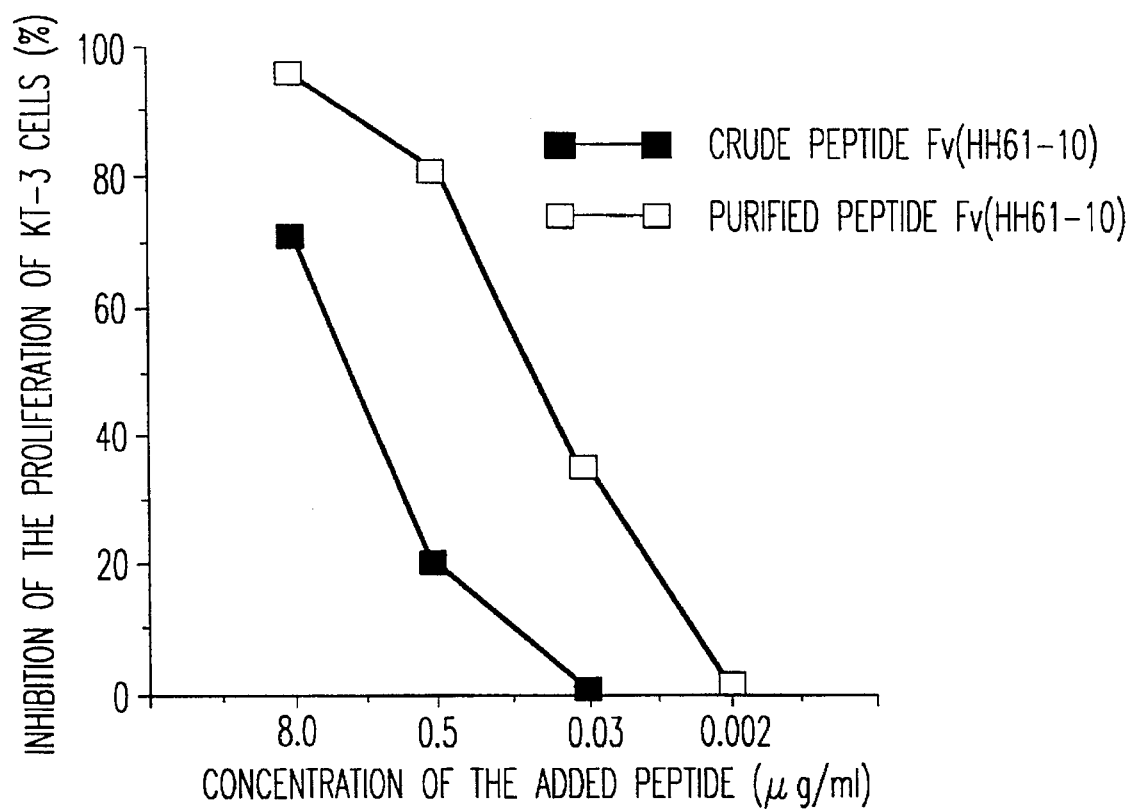
FIG. 6 shows the inhibition of the IL-6-dependent growth of KT-3 cells by the peptide Fv(HH61-10)

The peptide Fv(HH61-10) diluted to an appropriate concentration with an RPMI1640 medium containing 10% FCS was mixed with 0.4 ng/ml of human recombinant IL-6, and these were reacted at 37° C. for 30 minutes. After the reaction, $5 \times 10^3$ KT-3 cells suspended in the same medium were added thereto and cultured at 37° C. for 2 days. After the culturing, an MTT reagent (product of Sigma Co.) prepared in the same medium to a concentration of 5 mg/ml was added thereto for further culturing at 37° C. for 4 hours, after which the cells were dissolved with isopropanol containing 0.04N HCl, and the absorbance of the solution at 570 nm was measured to determine the viable cell count. As a result, as shown in FIG. 6, it was clear that the peptide Fv(HH61-10) inhibits the IL-6-dependent growth of KT-3 cells. That is, this peptide Fv(HH61-10) was shown to be a useful substance for the treatment of diseases such as multiple myeloma, rheumatoid arthritis, mesangial proliferative glomerulonephritis and the like, which are caused by the IL-6-induced abnormal growth of cells.

(3) Inhibiting activity against acute phase protein production induced by IL-6

Figure 7:
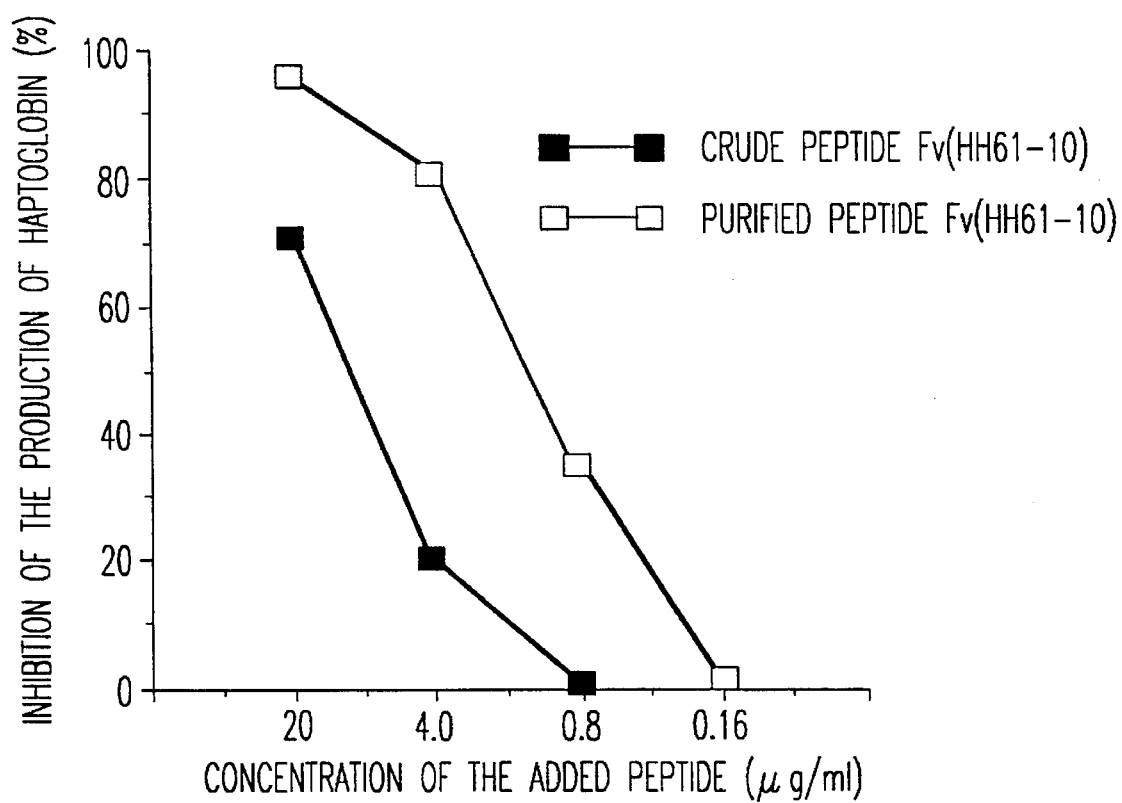
FIG. 7 shows the inhibition of the IL-6-dependent haptoglobin production by Hep3B cells by the peptide Fv(HH61-10) .

The peptide Fv(HH61-10) diluted to an appropriate concentration with a Dulbecco modified Eagle medium containing 10% FCS (product of Gibco Co.) was mixed with 100 ng/ml of human recombinant IL-6, and these were reacted at 37° C. for 30 minutes. After the reaction, the mixture was reacted with Hep3B cells which had precultured in the same medium at 37° C. for 16 hours at an initial population of $1 \times 10^4$ cells per well, and these were further cultured at 37° C. for 2 days. Next, each of the culture supernatants was taken out its well, and the haptoglobin contents thereof were assayed by the ELISA method. The ELISA method comprised first coating sheep anti-human haptoglobin antibody (product of Binding Site Co.) dissolved in PBS to a concentration of 1 µg/ml into each well of a 96-well plate (product of Flow Co.) and reacting them at 4° C. overnight. After the reaction, a PBS solution containing 0.5% BSA was added to the mixture which was then allowed to stand at room temperature for 1 hour. The PBS solution containing 0.5% BSA was discarded, and then each culture supernatant diluted 4-fold with the same type of solution was added to the residue for reaction at room temperature for 2 hours. After the reaction, the solution was washed 3 times with a PBS solution containing 0.05% Tween20, and alkali phosphatase-labelled sheep anti-human haptoglobin antibody (product of Binding Site Co.) which had been diluted 1,000-fold with a PBS solution containing 0.5% BSA was added thereto, for reaction at room temperature for 2 hours. After the reaction, the solution was washed 3 times with a PBS solution containing 0.05% Tween20, p-nitrophenol phosphate (product of Sigma Co.) adjusted to a concentration of 1 mg/ml with a 0.1M carbonate buffer solution (pH 9.6) was added to the mixture which was then allowed to stand for 15 minutes, and then the absorbance at 405 nm was measured. As a result, as shown in FIG. 7, it was clear that the peptide Fv(HH61-10) inhibits the IL-6-induced production of haptoglobin, a type of acute phase protein, by Hep3B cells. That is, this peptide Fv(HH61-10) was shown to be a useful substance for the treatment of inflammatory diseases.

As mentioned above, the peptide according to the present invention inhibits the binding of human IL-6 to human IL-6 receptor and suppresses the activity of human IL-6, and thus it is an effective substance for use as a treatment for autoimmune diseases such as rheumatoid arthritis and systemic lupus erythematosus, a treatment for bacterial infections, a treatment for septic shock due to bacterial infections, a treatment for viral infections, a treatment for cancers such as multiple myeloma, a cancer metastasis suppressant, a medicine for the amelioration of cancer cachexia, and a treatment for inflammatory diseases such as mesangial proliferative glomerulonephritis, and other diseases thought to be induced or aggravated by IL-6.

This application is based on Japanese Patent Application 028173/1993, filed Feb. 17, 1993, which is incorporated herein by reference.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent in the United States is:

1. A single chain peptide which has the amino acid sequence shown in SEQ ID NO:7.
2. A single chain peptide which has the amino acid sequence shown in SEQ ID NO:7 with the N-terminal Met removed.
3. A pharmaceutical composition comprising a pharmaceutically acceptable carrier and a single chain peptide having the amino acid sequence shown in SEQ ID NO:7.
4. A pharmaceutical composition comprising a pharmaceutically acceptable carrier and a single chain peptide having the amino acid sequence shown in SEQ ID NO:7 with the N-terminal Met removed.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
 ( A ) LENGTH: 23 base pairs
 ( B ) TYPE: nucleic acid
 ( C ) STRANDEDNESS: single
 ( D ) TOPOLOGY: linear ( i i ) MOLECULE TYPE: Other nucleic acid;
 ( A ) DESCRIPTION: DNA (synthetic)

( x i ) SEQUENCE DESCRIPTION: SEQ ID NO:1:

CAGGTSMARC TCGAGSAGTC WGG         23

( 2 ) INFORMATION FOR SEQ ID NO:2:

( i ) SEQUENCE CHARACTERISTICS:
 ( A ) LENGTH: 32 base pairs
 ( B ) TYPE: nucleic acid
 ( C ) STRANDEDNESS: single
 ( D ) TOPOLOGY: linear ( i i ) MOLECULE TYPE: Other nucleic acid;
 ( A ) DESCRIPTION: DNA (synthetic)

( x i ) SEQUENCE DESCRIPTION: SEQ ID NO:2:

AAGCTTCATG AGGAGACGGT GACCGTGGTC CC                                32

( 2 ) INFORMATION FOR SEQ ID NO:3:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: DNA (synthetic)

( x i ) SEQUENCE DESCRIPTION: SEQ ID NO:3:

ACAGTCATAA TGTCCCATAT GGA Y AT Y CWG MTGACMCAGT CTCCA               45

( 2 ) INFORMATION FOR SEQ ID NO:4:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: DNA (synthetic)

( x i ) SEQUENCE DESCRIPTION: SEQ ID NO:4:

GCATCGTCGA CTTTGAGCTC CAGCTTGGTC CC                                32

( 2 ) INFORMATION FOR SEQ ID NO:5:

( i ) SEQUENCE CHARACTERISTICS:
        ( A ) LENGTH: 87 base pairs
        ( B ) TYPE: nucleic acid
        ( C ) STRANDEDNESS: double
        ( D ) TOPOLOGY: linear ( i i ) MOLECULE TYPE: Other nucleic acid;
        ( A ) DESCRIPTION: DNA (synthetic)

( x i ) SEQUENCE DESCRIPTION: SEQ ID NO:5:

CGATTAGTAA GGAGGTTTCA TATGTCGACA AATCCTCAGG ATCTGGCTCC GAATCCAAAA   60

GCACGCAGGT CAAACTCGAG AAGCTTG                                      87

( 2 ) INFORMATION FOR SEQ ID NO:6:

( i ) SEQUENCE CHARACTERISTICS:
        ( A ) LENGTH: 738 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: DNA (synthetic)

( i x ) FEATURE:
        ( A ) NAME/KEY: CDS
        ( B ) LOCATION: 1..738

( x i ) SEQUENCE DESCRIPTION: SEQ ID NO:6:

```
ATG GAC ATC CTG CTG ACA CAG TCT CCA AAA TTC CTG CTT GTA TCA GCA    48
Met Asp Ile Leu Leu Thr Gln Ser Pro Lys Phe Leu Leu Val Ser Ala
 1               5                  10                  15

GGA GAC AGG GTT ACC ATA ACC TGC AAG GCC AGT CAG AGT GTG AGT ACT    96
Gly Asp Arg Val Thr Ile Thr Cys Lys Ala Ser Gln Ser Val Ser Thr
            20                  25                  30
```

| | | | | | | | | | | | | | | | | |
|---|---|---|---|---|---|---|---|---|---|---|---|---|---|---|---|---|
| GAT | GTA | AGT | TGG | TAC | CAA | CAG | AAG | CCA | GGG | CAG | TCT | CCT | AAA | CTA | CTG | 144 |
| Asp | Val | Ser | Trp | Tyr | Gln | Gln | Lys | Pro | Gly | Gln | Ser | Pro | Lys | Leu | Leu | |
| | | 35 | | | | 40 | | | | | 45 | | | | | |
| ATA | TAC | TAT | GCA | TCC | AAT | CGC | TAC | ACT | GGA | GTC | CCT | GAT | CGC | TTC | ACT | 192 |
| Ile | Tyr | Tyr | Ala | Ser | Asn | Arg | Tyr | Thr | Gly | Val | Pro | Asp | Arg | Phe | Thr | |
| | 50 | | | | | 55 | | | | | 60 | | | | | |
| GGC | AGT | GGA | TAT | GGG | ACG | GAT | TTC | ACT | TTC | ACC | ATC | AGC | ACT | GTG | CAG | 240 |
| Gly | Ser | Gly | Tyr | Gly | Thr | Asp | Phe | Thr | Phe | Thr | Ile | Ser | Thr | Val | Gln | |
| 65 | | | | 70 | | | | | 75 | | | | | | 80 | |
| GCT | GAA | GAC | CTG | GCA | GTT | TAT | TTC | TGT | CAG | CAG | GAT | TAT | AGG | TCT | CCA | 288 |
| Ala | Glu | Asp | Leu | Ala | Val | Tyr | Phe | Cys | Gln | Gln | Asp | Tyr | Arg | Ser | Pro | |
| | | | | 85 | | | | | 90 | | | | | 95 | | |
| TTC | ACG | TTC | GGC | TCG | GGG | ACA | AAG | TTG | GAA | ATA | AAA | GTC | GAC | AAA | TCC | 336 |
| Phe | Thr | Phe | Gly | Ser | Gly | Thr | Lys | Leu | Glu | Ile | Lys | Val | Asp | Lys | Ser | |
| | | | 100 | | | | | 105 | | | | 110 | | | | |
| TCA | GGA | TCT | GGC | TCC | GAA | TCC | AAA | AGC | ACG | CAG | GTC | AAA | CTC | GAG | GAG | 384 |
| Ser | Gly | Ser | Gly | Ser | Glu | Ser | Lys | Ser | Thr | Gln | Val | Lys | Leu | Glu | Glu | |
| | | 115 | | | | | 120 | | | | | 125 | | | | |
| TCT | GGC | CCT | GGG | ATA | TTG | CAG | CCC | TCC | CAG | ACC | CTC | AGT | CTG | ACT | TGT | 432 |
| Ser | Gly | Pro | Gly | Ile | Leu | Gln | Pro | Ser | Gln | Thr | Leu | Ser | Leu | Thr | Cys | |
| | 130 | | | | | 135 | | | | | 140 | | | | | |
| TCT | TTC | TCT | GGG | TTT | TCA | CTG | AGC | ACT | TCT | GGT | ATG | GGT | GTG | AGC | TGG | 480 |
| Ser | Phe | Ser | Gly | Phe | Ser | Leu | Ser | Thr | Ser | Gly | Met | Gly | Val | Ser | Trp | |
| 145 | | | | | 150 | | | | | 155 | | | | | 160 | |
| ATT | CGT | CAG | CCT | TCA | GGG | AAG | GGT | CTG | GAG | TGG | CTG | GCA | CAC | ATT | TAT | 528 |
| Ile | Arg | Gln | Pro | Ser | Gly | Lys | Gly | Leu | Glu | Trp | Leu | Ala | His | Ile | Tyr | |
| | | | | 165 | | | | | 170 | | | | | 175 | | |
| TGG | GAT | GAT | GAC | AAA | CAC | TAT | AAC | CCA | TCC | CTG | AAG | AGC | CGG | CTC | ACA | 576 |
| Trp | Asp | Asp | Asp | Lys | His | Tyr | Asn | Pro | Ser | Leu | Lys | Ser | Arg | Leu | Thr | |
| | | | 180 | | | | | 185 | | | | | 190 | | | |
| ATC | TCC | AAG | GAT | ACC | TCC | ACC | AAC | CAG | GTA | TTC | CTC | AAG | ATC | ACC | AGT | 624 |
| Ile | Ser | Lys | Asp | Thr | Ser | Thr | Asn | Gln | Val | Phe | Leu | Lys | Ile | Thr | Ser | |
| | | 195 | | | | | 200 | | | | | 205 | | | | |
| GTG | GAC | ACT | GCA | GAT | ACT | GCC | ACA | TAC | TTC | TGT | GCT | CGA | AGA | AGT | CTC | 672 |
| Val | Asp | Thr | Ala | Asp | Thr | Ala | Thr | Tyr | Phe | Cys | Ala | Arg | Arg | Ser | Leu | |
| | 210 | | | | | 215 | | | | | 220 | | | | | |
| TAT | GGT | AAT | TGG | GGG | GAC | TAT | GCT | ATG | GAC | TAC | TGG | GGT | CAA | GGA | ACC | 720 |
| Tyr | Gly | Asn | Trp | Gly | Asp | Tyr | Ala | Met | Asp | Tyr | Trp | Gly | Gln | Gly | Thr | |
| 225 | | | | 230 | | | | | 235 | | | | | 240 | | |
| TCA | GTC | ACC | GTC | TCC | TCA | | | | | | | | | | | 738 |
| Ser | Val | Thr | Val | Ser | Ser | | | | | | | | | | | |
| | | | | 245 | | | | | | | | | | | | |

( 2 ) INFORMATION FOR SEQ ID NO:7:

( i ) SEQUENCE CHARACTERISTICS:
        ( A ) LENGTH: 246 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

| | | | | | | | | | | | | | | | |
|---|---|---|---|---|---|---|---|---|---|---|---|---|---|---|---|
| Met | Asp | Ile | Leu | Leu | Thr | Gln | Ser | Pro | Lys | Phe | Leu | Leu | Val | Ser | Ala |
| 1 | | | | 5 | | | | | 10 | | | | | 15 | |
| Gly | Asp | Arg | Val | Thr | Ile | Thr | Cys | Lys | Ala | Ser | Gln | Ser | Val | Ser | Thr |
| | | | 20 | | | | | 25 | | | | | 30 | | |
| Asp | Val | Ser | Trp | Tyr | Gln | Gln | Lys | Pro | Gly | Gln | Ser | Pro | Lys | Leu | Leu |
| | | 35 | | | | | 40 | | | | | 45 | | | |
| Ile | Tyr | Tyr | Ala | Ser | Asn | Arg | Tyr | Thr | Gly | Val | Pro | Asp | Arg | Phe | Thr |
| | 50 | | | | | 55 | | | | | 60 | | | | |

| | | | | | | | | | | | | | | | |
|---|---|---|---|---|---|---|---|---|---|---|---|---|---|---|---|
| Gly 65 | Ser | Gly | Tyr | Gly | Thr 70 | Asp | Phe | Thr | Phe 75 | Thr | Ile | Ser | Thr | Val | Gln 80 |
| Ala | Glu | Asp | Leu | Ala 85 | Val | Tyr | Phe | Cys | Gln 90 | Gln | Asp | Tyr | Arg | Ser 95 | Pro |
| Phe | Thr | Phe | Gly 100 | Ser | Gly | Thr | Lys | Leu 105 | Glu | Ile | Lys | Val | Asp 110 | Lys | Ser |
| Ser | Gly | Ser 115 | Gly | Ser | Glu | Ser | Lys 120 | Ser | Thr | Gln | Val | Lys 125 | Leu | Glu | Glu |
| Ser | Gly 130 | Pro | Gly | Ile | Leu | Gln 135 | Pro | Ser | Gln | Thr | Leu 140 | Ser | Leu | Thr | Cys |
| Ser 145 | Phe | Ser | Gly | Phe | Ser 150 | Leu | Ser | Thr | Ser | Gly 155 | Met | Gly | Val | Ser | Trp 160 |
| Ile | Arg | Gln | Pro | Ser 165 | Gly | Lys | Gly | Leu | Glu 170 | Trp | Leu | Ala | His | Ile 175 | Tyr |
| Trp | Asp | Asp | Asp 180 | Lys | His | Tyr | Asn | Pro 185 | Ser | Leu | Lys | Ser | Arg 190 | Leu | Thr |
| Ile | Ser | Lys 195 | Asp | Thr | Ser | Thr | Asn 200 | Gln | Val | Phe | Leu | Lys 205 | Ile | Thr | Ser |
| Val | Asp 210 | Thr | Ala | Asp | Thr | Ala 215 | Thr | Tyr | Phe | Cys | Ala 220 | Arg | Arg | Ser | Leu |
| Tyr 225 | Gly | Asn | Trp | Gly | Asp 230 | Tyr | Ala | Met | Asp | Tyr 235 | Trp | Gly | Gln | Gly | Thr 240 |
| Ser | Val | Thr | Val | Ser 245 | Ser | | | | | | | | | | |